(12) United States Patent
Burrell et al.

(10) Patent No.: US 6,486,383 B1
(45) Date of Patent: *Nov. 26, 2002

(54) MODIFICATION OF STARCH CONTENT IN PLANTS

(75) Inventors: Michael Meyrick Burrell, Cottenham (GB); Stephen Andrew Coates, Cambridge (GB); Alfhous Freddie Weir, Cambridge (GB)

(73) Assignee: Advanced Technologies (Cambridge) Limited, London (GB)

( * ) Notice: Subject to any disclaimer, the term of this patent is extended or adjusted under 35 U.S.C. 154(b) by 13 days.

This patent is subject to a terminal disclaimer.

(21) Appl. No.: 09/615,557

(22) Filed: Jul. 13, 2000

Related U.S. Application Data

(63) Continuation of application No. 08/750,843, filed as application No. PCT/GB95/01307 on Jun. 6, 1995, now Pat. No. 6,096,945.

(30) Foreign Application Priority Data

Jun. 16, 1994 (GB) .............................................. 9412018

(51) Int. Cl.$^7$ ........................ C12N 15/82; C12N 15/29; C12N 15/54; A01H 5/00; C12P 19/04
(52) U.S. Cl. ...................... 800/284; 800/278; 800/313; 800/317.2; 800/317.4; 800/320; 800/320.1; 800/320.2; 800/320.3; 435/69.1; 435/101; 435/194; 435/468
(58) Field of Search ................................ 800/278, 284, 800/317.2, 317.4, 313, 320, 320.1, 320.2, 320.3; 435/69.1, 101, 194, 468

(56) References Cited

U.S. PATENT DOCUMENTS

| | | |
|---|---|---|
| 5,498,832 A | 3/1996 | Gausing et al. |
| 5,792,920 A | 8/1998 | Bridges |

FOREIGN PATENT DOCUMENTS

| | | |
|---|---|---|
| EP | 0 368 506 | 5/1990 |
| WO | WO 93/09237 | * 5/1993 |
| WO | WO 94/24292 | 10/1994 |
| WO | WO 94/28146 | 12/1994 |
| WO | WO 94/28149 | 12/1994 |
| WO | WO 95/09242 | 4/1995 |

OTHER PUBLICATIONS

Ainsworth et al. Plant Mol. Biol. 23: 23–33, 1993.*
Anderson et al., 1989, "The Encoded Primary Sequence of a Rice Seed ADP–Glucose Pyrophosphorylase Subunit and Its Homology to the Bacterial Enzyme", J. Biol. Chem. 264: 12238–12242.
Bae et al., 1990, "Cloning and Characterization of the Brittle–2 Gene of Maize", Maydica 35:317–322.
Baecker et al., 1983, "Biosynthesis of Bacterial Glycogen", J. Biol. Chem. 258:5084–5088.
Bhave et al., 1990, "Identification and Molecular Characterization of Shruken–2 cDNA Clones of Maize", The Plant Cell 2:581–588.
Blakeley et al., 1990, "Cloning and Characterization of a cDNA for the Cytosolic Isozyme of Plant Pyruvate Kinase: the Relationship Between the Plant and Non–Plant Enzyme", Plant Mol. Biol. 15:665–669.
Burke et al., 1983, "The Isolation, Characterization and Sequence of the Pyruvate Kinase Gene of *Saccharomyces cerevisiae*", J. Biol. Chem 258:2193–2201.
Carabaza et al., 1990, "Purification, Characterization and Partial Amino Acid Sequence of Glycogen Synthase from *Saccharomyces cerevisiae*", Biochem. J. 268:401–407.
Carlisle et al., 1990, "Pyrophosphate–Dependent Phosphofructokinase", J. Biol. Chem. 265:18366–18371.
Daldal, 1984, "Nucleotide Sequence of Gene pfkB Encoding the Minor Phosphofructokinase of *Escherichia coli* K–12", Gene 28:337–342.
Geiser et al., 1980, "A cDNA Clone from *Zea mays* Endosperm Sucrose Synthetase mRNA", Nucl. Acids Res. 8:6175–6188.
Gupta et al., 1988, "Complementary DNA of Two Non–Allelic Sucrose Synthase Genes in Maize: Cloning, Expression, Characterization and Molecular Mapping of the Sucrose Synthase Gene", Plant Mol. Biol. 10:215–224.
Heinisch et al., 1989, "The Phosphofructokinase Genes of Yeast Evolved from Two Duplication Events", Gene 78:309–321.
Hellinga and Evans, 1985, "Nucleotide Sequences and High–Level Expression of the Major *Escherichia coli* Phosphofructokinase", Eur. J. Biochem. 149:363–373.
Johnson et al., "Distinct Sequence Determinants Direct Intracellular Sorting and Modification of a Yeast Vacuolar Protease", Cell 48:875–885.
Lee et al., 1987, "Amino Acid Sequence of an *escherichia coli* ADPglucose Synthetase Allosteric Mutant as Deduced form the DNA Sequence of the gig C Gene", Nucl. Acids Res. 15:10603.
Lee et al., 1987 "The Rabbit Muscle Phosphofructokinase Gene", J. Biol. Chem. 262:4195–4199.
McCarty et al., 1986, "The Cloning, Genetic Mapping, and Expression of the Constitutive Sucrose Synthase Locus of Maize", Proc. Natl. Acad. Sci. USA 83:9099–9013.
Müller–Röber et al., 1990, "One of Two Different ADP–Glucose Pyrophosphorylase Genes from Potato Responds Strongly to Elevated Levels of Sucrose", Mol. Gen. Genet. 224:136–146.

(List continued on next page.)

Primary Examiner—David T. Fox
(74) Attorney, Agent, or Firm—Pennie & Edmonds LLP

(57) ABSTRACT

The present invention relates to a transgenic plant which comprises a recombinant gene encoding one of the subunit proteins of adenosine diphosphoglucose pyrophosphorylase ("ADPG PPase"). In plants, functional ADPG PPase holoenzyme is a heterotetrameric protein composed of two subunits, each encoded by a different gene. The present invention shows that the activity of ADPG PPase in the cell of plants can be increased by expressing only one of the two subunit proteins required to make an active enzyme.

10 Claims, 4 Drawing Sheets

OTHER PUBLICATIONS

Ohara et al., 1989, "Direct Genomic Sequencing of Bacterial DNA: the Pyruvate Kinase I Gene of *Escherichia coli*", Proc. Natl. Acad. Sci. USA 86:6883–6887.

Olive et al., 1989 "Isolation and Nucleotide Sequences of cDNA Clones Encoding ADP_Glucose Pyrophosphorylase Polypeptides from Wheat Leaf and Endosperm", Mol. Biol. 12:525–538.

Rohde et al., 1990, "Structural and Functional Analysis of Two Waxy Gene Promoters from Potato", Genet. & Breed. 44:311–315.

Rohde et al., 1988, "Structural Analysis of the *waxy* Locus from *Hordeum vulgare*", Nucl. Acids Res. 16:7185–7186.

Salanoubat and Belliard, 1987, "Molecular Cloning and Sequencing of Sucrose Synthase cDNA from Potato *(Solanum tuberosum*L.): Preliminary Characterization of Sucrose Synthase mRNA Distribution", Gene 60:47–56.

Takenaka et al., 1989, "Rat Pyruvate Kinase M Gene", J. Biol. Chem. 264:2363–2367.

Taussig et al., 1983, "Nucleotide Sequence of the Yeast SUC2 Gene for Invertase", Nucl. Acids Res. 11:1943–1955.

Visser et al., 1989, "Molecular Cloning and Partial Characterization of the Gene for Granule–Bound Starch Synthase from a Wildtype and an Amylose–Free Potato (*Solanum tuberosum* L.)", Plant Sci. 64:185–192.

Von Schaewen et al., 1990, "Expression of a Yeast–Derived Invertase in the Cell Wall of Tobacco and Arabidopsis Plants Yields to Accumulation of Carbohydrate and Inhibition of Photosynthesis and Strongly Influences Growth and Phenotype of Transgenic Tobacco Plants", EMBO J. 9:3033–3044.

Werr et al., 1985, "Structure of the Sucrose Synthase Gene on Chromosome 9 of *Zea mays* L.", EMBO J. 4:1373–1380.

Witt and Sauter, 1994, "Enzymes of Starch Metabolism in Poplar Wood During Fall and Winter", J. Plant Physiol. 143:625–631.

Worrell et al., 1991, "Expression of a Maize Sucrose Phosphate Synthase in Tomato Alters Leaf Carbohydrate Partitioning", The Plant Cell 3:1121–1130.

Zack et al., 1986, "DNA Sequence of a Shrunken Allele of Maize: Evidence for Visitation by Insertional Sequences", Maydica 31:5–16.

Lin et al., 1995, The gene structure of starch phosphorylase from sweet potato, Plant Physiol, Jan., 107:277–8.

Rahmatullah et al., 1989, Nucleotide and predicted amino acid sequences of two different genes of high–pI –amylases from barley, Plant Mol. Biol., 12, 119–121.

* cited by examiner

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 27 base pairs
      (B) TYPE: nucleic acid
      (C) STRANDEDNESS: unknown
      (D) TOPOLOGY: unknown (ii) MOLECULE TYPE: Other (xi) SEQUENCE DESCRIPTION: SEQ ID NO: 1:

ATAATCATCG CAAGACCGGC AACAGGA      27

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: unknown
      (D) TOPOLOGY: unknown (ii) MOLECULE TYPE: Other (xi) SEQUENCE DESCRIPTION: SEQ ID NO: 2:

CCTCGTCAGG GGATACAATC TAGTCCC      27

(2) INFORMATION FOR SEQ ID NO: 3:

(i) SEQUENCE CHARACTERISTICS:
      (A) LENGTH: 23 base pairs
      (B) TYPE: nucleic acid
      (C) STRANDEDNESS: unknown
      (D) TOPOLOGY: unknown (ii) MOLECULE TYPE: Other (xi) SEQUENCE DESCRIPTION: SEQ ID NO: 3:

-continued

```
CACCAACAAA ATTTCGCGGA TCC                                      23
```

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO: 4:

```
CAGACCATGC TATTTGTTG                                           19
```

MODIFICATION OF STARCH CONTENT IN PLANTS

This is a continuation of application Ser. no. 08/750,843 filed Feb. 6, 1997, now U.S. Pat. No. 6,096,945, which is a national stage application of PCT/GB95/01307 filed under 35 U.S.C. §371 on Jun. 6, 1995. These applications are incorporated by reference herein in its entirety.

BACKGROUND OF THE INVENTION

This invention relates to the modification of starch content of plants, and in particular, to the increase of starch content in plants.

Starch is a complex polymer of glucosyl residues. It is the major form in which carbohydrate is stored in the tissues of most species of higher plants. It is accumulated in the leaves of plants during the day as a result of photosynthesis and is used to supply the needs of the plant for energy and biosynthesis during the night. Starch is also accumulated in non-photosynthetic tissues, especially those involved in reproduction such as seeds, fruits and tubers. Therefore, starch is of great importance to the productivity of the plant and its survival.

Starch is also highly significant to man. Firstly, it forms a major component of animal diets, supplying man and his domestic animals with a large portion of their carbohydrate intake. Secondly, the type of starch in a plant affects the quality of the processed plant product. Thirdly, starch is used industrially in the production of paper, textiles, plastics and adhesives, as well as providing the raw material for some bio-reactors. Starch from different species have preferred uses. On a world scale, starch producing crops are agriculturally and economically by far the most important, and these crops include wheat, maize, rice and potatoes. The quantity of starch present in the harvested organ of a plant will affect the gross yield and the processing efficiency of the crop. In addition, the type of starch will affect the quality of a processed product and the profitability of the process.

Starch is synthesised in amyloplasts in plants from glucose-1-phosphate (Glc-1-P) as shown below.

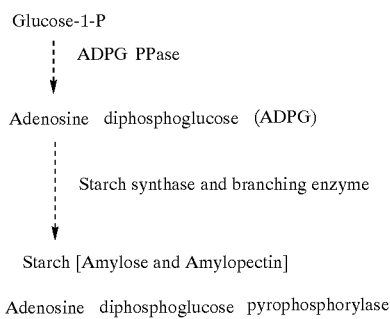

[EC.2.7.7.27] (ADPG PPase) catalyses the first committed step of the pathway of starch biosynthesis in plants. A similar enzyme catalysing the same reaction is found in bacteria and cyanobacteria.

The quaternary structure of the enzyme is similar in all organisms investigated in that the functional enzyme is composed of a tetramer of subunit proteins. In bacteria the protein subunits are identical and the product of a single gene, e.g. in *E. coli* the GlgC gene. In plants, however, the enzyme is composed of two each of two different protein subunits. While these different protein subunits display sequence similarities, they are the product of two distinct genes.

There are many mutants of plants that have a lower starch content in particular tissues compared to that of wild-type plants. These mutant plants are deficient in the expression of one of the genes coding for the subunits of ADPG PPase. Two particular mutations seen in maize endosperm are the mutants shrunken-2 and brittle-2. It is argued that the wild-type genes for these code for the two subunit proteins of the enzyme. Both mutations cause decreased enzyme activity of ADPG PPase in the endosperm. It is argued from this information that both subunits of the enzyme are required for full activity and that lack of a particular type of subunit cannot be compensated for by the other subunit.

This invention is based on the fact that one only of the genes for one of the subunit proteins of an enzyme catalysing starch production is required to increase enzyme activity.

It is an object of the present invention to provide a method for increasing the activity of an enzyme catalysing starch synthesis.

It is a further object of the present invention to provide a plant having an increased starch content when compared with a control plant not treated in accordance with the inventive method.

It is also an object of the invention to increase the rate of starch synthesis under conditions which do not lead to a compensating increase in the rate of starch breakdown.

SUMMARY OF THE INVENTION

The present invention provides a method of increasing the enzyme activity in a plant comprising introducing into a plant one of the genes of one of the subunit proteins of an enzyme catalysing starch synthesis, thereby causing expression of the subunit gene in the plant to produce the subunit protein, and an increase in the enzyme activity in the plant cells.

The present invention further provides a plant into which has been introduced one of the genes of one of the subunit proteins of an enzyme catalysing starch synthesis, which plant expresses the gene to produce a subunit protein, and increases the enzyme activity in the plant cells.

The method may also include introducing one of the genes of one of the subunit proteins of a plurality of other enzymes catalysing starch synthesis.

The present invention also provides a plasmid incorporating one of the genes of one of the subunit proteins of an enzyme catalysing starch synthesis in plants.

A plasmid or plant according to the invention may also contain one of the genes of one of the subunit proteins of one or more other enzymes catalysing starch synthesis in the plants.

The present invention also provides a plant cell harbouring a plasmid described above.

Preferably the gene is the brittle-2 gene or a homologue thereof. Advantageously the ;gene is the wheat brittle-2 gene.

Preferably the plant is grown commercially and is any one of maize, wheat, rice, potato, cassava, peanut, beans, carrots, tomato or tobacco crop for example.

Preferably ADPG PPase activity is increased by the method of the invention.

An increase in starch content, especially in potatoes, may be measured as an increase in specific gravity (S.G.) of the plant or tuber, for example.

Preferably the plasmid incorporates a homologue of the brittle-2 gene of an enzyme catalysing starch synthesis. Alternatively, the plasmid may incorporate a homologue of the shrunken-2 gene of an enzyme catalysing starch synthesis.

In order that the present invention may be easily understood and readily carried into effect reference will now be made to the following Example and the drawings,

DETAILED DESCRIPTION OF THE INVENTION

Transgenic potato plants were produced containing a gene from wheat which is homologous to the brittle-2 gene in maize. This gene is thus known as the wheat brittle-2 gene. We found that surprisingly expression of the brittle-2 gene in transgenic potato plants caused an increase in the ADPG PPase activity. It thus appears possible to increase the activity of this enzyme in the cell by expressing only one of the two subunit proteins required to make an active enzyme. When the activity of ADPG PPase is a major factor in limiting the amount of starch made or stored in a plant, then the expression of just brittle-2 protein provides a mechanism of increasing the amount of starch in the tuber and the specific gravity in the tuber, and possibly increasing the amount of starch in any plant that stores starch. This would improve the yield of starch from the plant and would be of great commercial value.

The transgenic potato plants transformed with the gene for the brittle-2 subunit of ADPG PPase from wheat were analysed to identify the presence of the subunit protein in the transgenic potato plants and the degree of enzyme (ADPG PPase) activity in the plants. The amount of starch in the plants can also be assessed. The standard methods used in these analyses are described below:

Production of Transgenic Potato Plants

Figure 1A:
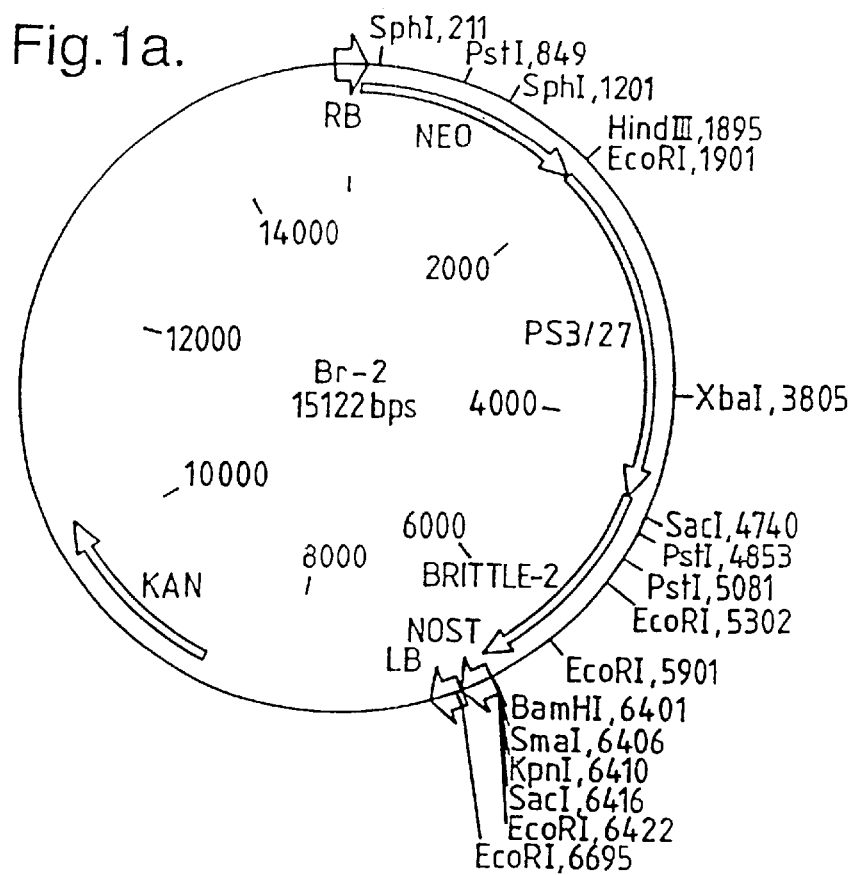
FIG. 1a shows a transformation vector or plasmid containing the brittle-2 gene.
Figure 1B:
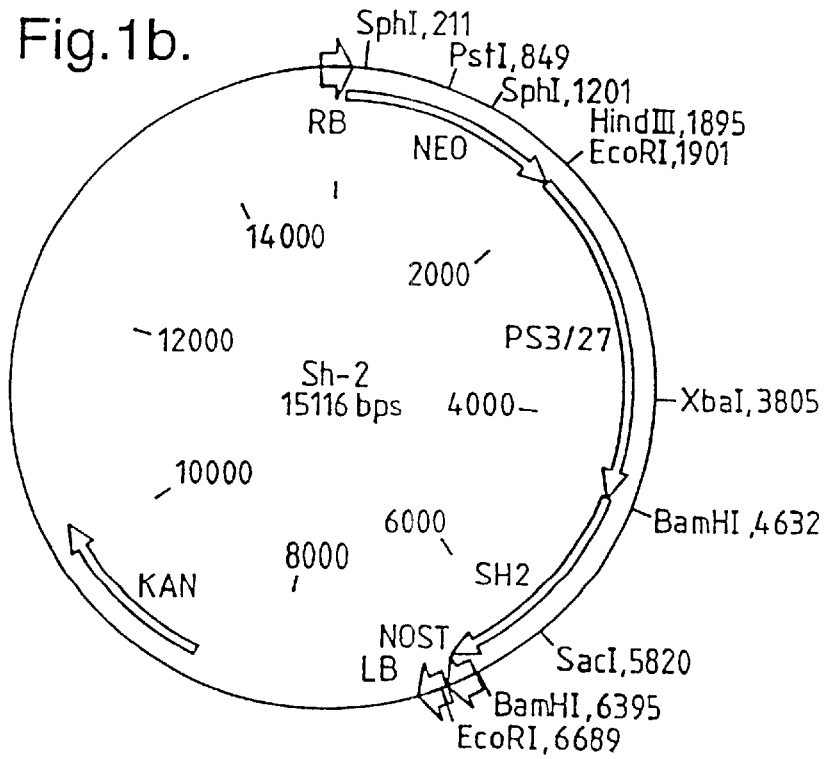
FIG. 1b shows a transformation vector or plasmid containing the shrunken-2 gene.

For the purpose of the present invention a coding sequence is selected which when expressed in transgenic plants causes an increase in ADPG PPase activity. The coding sequence may be from any plant. For the purpose of example the wheat homologue of the brittle-2 locus is chosen (Ainsworth, C; Tarvis, M; Clark, J. Pl. Mol. Biol. 23 23–33; 1993 Isolation and analysis of a cDNA encoding the small subunit of ADP-glucose pyrophosphorylase from wheat). This may be inserted into a transformation vector as shown in FIG. 1a. This plasmid pfW4091 was deposited under the Budapest treaty for the International Recognition of the Deposit of Micro-organisms for the purposes of Patent Procedure, at the National Collection of Industrial and Marine Bacteria on Jun. 13, 1994 under accession number NCIMB40649. The similar plasmid pfw 4151 containing the shrunken-2 coding sequence FIG. 1b was deposited on Jun. 13, 1994 under accession number NCIMB40650. The vector may therefore comprise one or more operative genes, a selectable marker gene and these may be introduced between the T-DNA borders. The operative genes consist of a promoter sequence to cause expression of the gene in tubers or other starch storing organs, tissues or cells, the coding sequence and the terminator sequence.

The vector is therefore typically provided with transcriptional regulatory sequences and/or, if not present at the 3'-end of the coding sequence of the gene, a stop codon. A DNA fragment may therefore also incorporate a terminator sequence and other sequences which are capable of enabling the gene to be expressed in plant cells. An enhancer or other element able to increase or decrease levels of expression obtained in particular parts of a plant or under certain conditions, may be provided in the DNA fragment and/or vector. The vector is also typically provided with an antibiotic resistance gene which confers resistance on transformed plant cells, allowing transformed cells, tissues and plants to be selected by growth on appropriate media containing the antibiotic.

Transformed plant cells can be selected by growth in an appropriate medium. Plant tissue can therefore be obtained comprising a plant cell which harbours a gene encoding an enzyme under the control of a promoter, for example in the plant cell genome. The gene is therefore expressible in the plant cell. Plants can then be regenerated which include the gene and the promoter in their cells, for example integrated in the plant cell genome such that the gene can be expressed. The regenerated plants can be reproduced and, for example, seed obtained.

A preferred way of transforming a plant cell is to use *Agrobacterium tumefaciens* containing a vector comprising a chimaeric gene as above. A hybrid plasmid vector may therefore be employed which comprises:

(a) a chimaeric gene containing regulatory elements capable of enabling the gene to be expressed when integrated in the genome of a plant cell;

(b) at least one DNA sequence which delineates the DNA to be integrated into the plant genome; and (c) a DNA sequence which enables this DNA to be transferred to the plant genome.

Typically the DNA to be integrated into the plant cell genome is delineated by the T-/DNA border sequences of a Ti-plasmid. If only one border sequence is present, it is preferably the right border sequence. The DNA sequence which enables the DNA to be transferred to the plant cell genome is generally the virulence (vir) region of a Ti-plasmid.

The gene coding for the polypeptide and its transcriptional and translational control elements can therefore be provided between the T-DNA borders of a Ti-plasmid. The plasmid may be a disarmed Ti-plasmid from which the genes for tumorigenicity have been deleted. The gene and its transcriptional control elements can, however, be provided between T-DNA borders in a binary vector in trans with a Ti-plasmid with a vir region. Such a binary vector therefore comprises:

(a) the chimaeric gene under the control of regulatory elements capable of enabling the gene to be expressed when integrated in the genome of a plant cell; and (b) at least one DNA sequence which delineates the DNA to be integrated into the plant genome.

*Agrobacterium tumefaciens,* therefore, containing a hybrid plasmid vector or a binary vector in trans with a Ti-plasmid possessing a vir region can be used to transform plant cells. Tissue explants such as stems or leaf discs may be inoculated with the bacterium. Alternatively, the bacterium may be co-cultured with regenerating plant protoplasts. Plant protoplasts or tissues may also be transformed by direct introduction of DNA fragments which encode the enzyme and in which the appropriate transcriptional and translational control elements are present or by a vector incorporating such a fragment. Direct introduction may be achieved using electroporation, polyethylene glycol, microinjection or particle bombardment.

Plant cells from angiospermous, gymnospermous, monocotyledonous or dicotyledonous plants can be transformed according to the present invention. Monocotyledonous species include barley, wheat, maize and rice. Dicotyledonous species include cotton, cassava, lettuce, melon pear petunia, potato, rape, soyabean, sugar beet, sunflower, tobacco and tomato. Potato cultivars to which the invention is applicable include Desiree, Maris Bard, Record, Russet Burbank, Atlantic and Pentland Dell.

Tissue cultures of transformed plant cells are propagated to regenerate differentiated transformed whole plants. The transformed plant cells may be cultured on a suitable medium, preferably a selectable growth medium. Plants may be regenerated from the resulting callus. Transgenic plants are thereby obtained whose cells incorporate the chimaeric gene in the genome, the chimaeric gene being expressible in the cells of the plants. Seed or other propagules from the regenerated plants can be collected for future use.

A preferred procedure in respect of the potato variety Record and Desiree is as follows.

Plant Material

Potato shoot cultures are maintained in vitro on Murashige and Skoog (MS) medium in Magenta GA-7 containers at 22° C. (16 h/8 h light/dark). These are nodally sub-cultured every 3 weeks.

In vitro shoots of 2–3 inches (5–7.5 cm) height are potted in 2.5 inches (6.4 cm) pots of Levingtons F1 compost. They are weaned in a propagator for one week in a growth room at 18° C. (16 h/8 h light/dark). The propagator is removed and the plants repotted at 3 weeks into 5 inch (12.7 cm) pots. At 5–7 weeks the plants are used for tranformation.

Agrobacterium tumefaciens

Liquid overnight cultures of suitable strains, e.g. LBA4404, C58#3 are grown at 28° C. to an $OD_{600}$ of 0.8 in L-broth (see appendix).

Cocultivation

The youngest four most expanded leaves are taken and surface sterilised in 10% Domestos (commercial bleach) for 15 minutes. Leaves are rinsed thoroughly with sterile water and then cut into discs with a 7mm cork borer. The discs are mixed with the Agrobacterium for 1–5 minutes, blotted dry on filter paper (Whatman No. 1) and then placed on callusing medium (see appendix) in 90 mm triple vented petri dishes, lower epidermis down. The 90 mm triple vented petri dishes are sealed with tape, cut to allow gas exchange and then incubated at 22° C./(16 h/8 h light/dark). The discs are transferred to callusing medium plus 50 $\mu$g ml$^{-1}$ of claforan and 30 $\mu$g ml$^{-1}$ kanamycin after 48 hours. This removes bacteria and selects for transformed cells.

Regeneration of Transformed Shoots

After 1 week, the discs are transferred to shooting medium (see appendix) containing the same antibiotics. Further transfers are made onto the same medium until shoots can be excised (usually about 4 weeks). Shoots with calli are transferred to MS medium with cefotaxime (500 $\mu$g/ml) in well ventilated containers, e.g. Magenta. Transformants are maintained, after several passages with cefotaxime to remove bacteria, on MS medium. They may be removed from in vitro, weaned and grown to maturity as described for the stock-plants. The process yields transformed potato plants at a frequency of up to 30% of the discs cocultivated.

APPENDIX

| | |
|---|---|
| L-broth | 10 g l$^{-1}$ bactotryptone |
| | 5 g l$^{-1}$ yeast extract |
| | 5 g l$^{-1}$ sodium chloride |
| | 1 g l$^{-1}$ glucose |
| Callusing medium | MS with 3% sucrose |
| | 0.5 mg l$^{-1}$ 2,4-D |
| | 2.5 mg l$^{-1}$ BAP |
| Shooting medium | MS plus 3% sucrose |
| | 2.5 mg l$^{-1}$ BAP |
| | 1.0 mg l$^{-1}$ GA$_3$ |

Identification of Wheat Brittle-2 Gene and Expression in Transgenic Plants

A southern blot was prepared with potato DNA extracted from lines transformed with NCIMB 40649 and lines transformed with NCIMB 40649 and NCIMB 40650 together. The extracted plant DNA was restricted with HindIII and 10 $\mu$g of DNA was used per track of the 1% agarose gel. The blot was probed with the brittle-2 coding sequence obtained from BamHI restricted plasmid DNA of NCIMB 40649. The blot was hybridised overnight at 55° C. in 5×SSC. After washing to a stringency of 0.2×SSC at 55° C. the blot was autoradiographed. The result shown in FIG. 2a indicates that between one and four copies of the brittle-2 gene had been introduced into the plants.

Figure 2A:
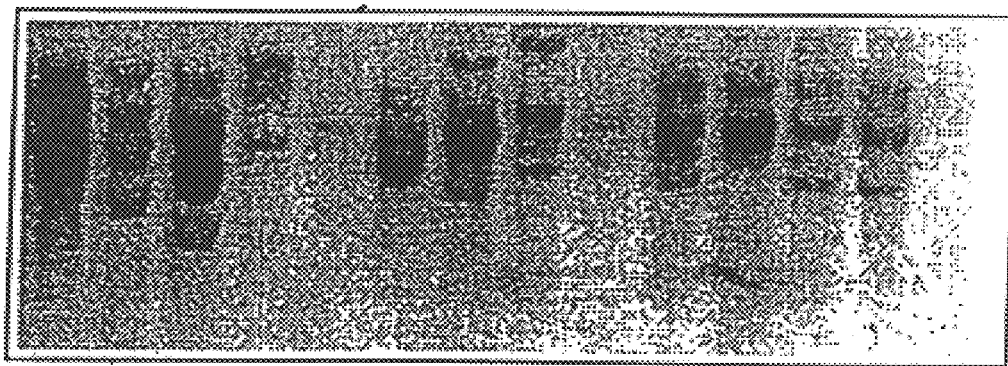
FIG. 2a shows a Southern blot of DNA extracted from treated and untreated plants.

In FIG. 2a lanes 1–4 are of DNA extracted from plants transformed with both the brittle-2 and shrunken-2 genes. Lanes 5–13 show DNA extracted from lines independently transformed with just the brittle-2 gene. Lane 14 shows DNA from an untransformed potato plant.

To show that DNA was expressed as message RNA oligonucleotide primers were prepared for the procedure known as RT-PCR which was performed on mRNA extracted from tubers of transformed potato plants. RT-PCR was performed on mRNA extracted from tuber material by the method described by Shirzadegan et al. (Nucleic acid research 19 6055; 1991 An efficient method of isolation of RNA from tissue cultured plant cells). The mRNA was treated with DNAse to remove contaminating DNA. For first strand synthesis the primer ATA ATC ATC GCA AGA CCG GCA ACA GGA (SEQ ID NO: 1) was used at 42° C. for 100 minutes. After removal of RNA with RNAse the second strand was synthesised to obtain a fragment at the 5' end and a fragment at the 3' end of the brittle-2 cDNA. To amplify the 5' end the primers CCT CGT CAG GGG ATA CAA TCT AGT CCC (SEQ ID NO: 2) and CAC CAA CAA AAT TTC GCG GAT CC (SEQ ID NO: 3) were used and to amplify the 3' end the primers CAG ACC ATG CTA TT GTT G (SEQ ID NO: 4) and ATA ATC ATC GCA AGA CCG GCA ACA (SEQ ID NO: 1) GGA were used. The conditions of amplification were of 24 cycles of 1 minute at 94° C., 30 seconds at 5° C., and 3 minutes at 72° C. After separation of the products on a 1% agarose gel and Southern blotting the blot was probed as described above. The results in FIG. 2b show that the introduced gene was expressed as mRNA.

Figure 2B:
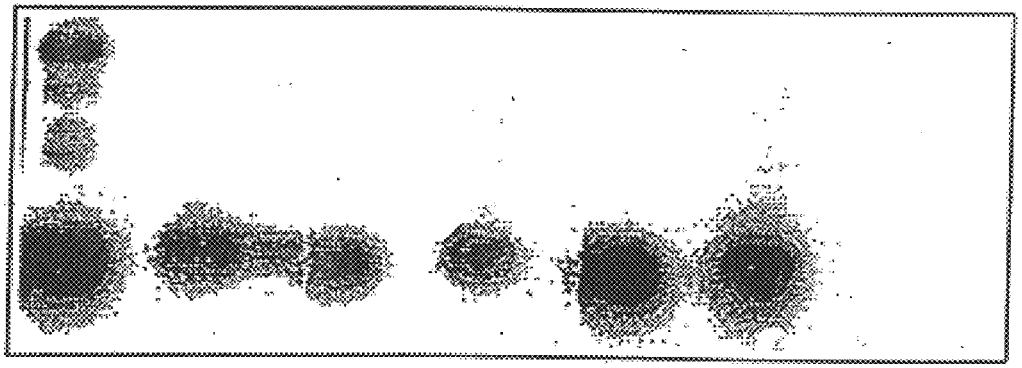
FIG. 2b shows a Northern blot of RT-PCR products from treated and untreated plants.

In FIG. 2b lanes 1–4, 5–8, 9–12 show RT-PCR products from three lines transformed with the brittle-2 sequence. Even numbered lanes show reactions lacking reverse transcriptase to indicate DNA contamination of the RNA. Lanes 1, 2, 5, 6, 9 and 10 show amplification of the 3' end and lanes 3, 4, 7, 8, 11, 12 show amplification of the 5' end. When no RNA or a non-transgenic plant was used as a control, no signal was obtained.

Production of Antisera to Indentify ADPG PPASE In Plants

1. Preparation of Proteins from *E. Coli* Expression Vectors

*E. coli* cells, transformed with GEX2T (Phamacia Ltd) expression constructs were grown up in the following way: A 1l-flask containing 100 ml of LB broth (10 g/l tryptone; 5 g/l yeast extract; 10 g/l sodium chloride (NaCl)) with 100 µg/ml ampicillin added, was inoculated with 20 µl of *E. coli* cells, and grown overnight at 37° C. The overnight culture was transferrred into a 5l-flask containing 900 ml of LB broth and grown on for 1 hour. The cells were induced to express the fusion protein by adding isopropyl Beta-D-thiogalactopyranoside (IPTG) to a final concentration of 1 mM. After growing for a further 4 hours the cells were harvested by centrifuging at 7000 rpm for 10 minutes. Pelleted cells were stored at −80° C. prior to extraction.

The pelleted cells were resuspended in 90 ml of ice cold 50 mM N-tris(hydroxmethyl)aminoethane (Tris), 150 mM NaCl, pH 8.0, placed in a glass beaker and sonicated for 45 seconds. Triton X-100 was added to a final concentration of 1%, and the extract clarified by centrifuging for 20 minutes at 10,000 rpm and 4° C. After centrifuging, the supernatant was decanted into a 250 ml-plastic bottle and 2–3 ml of a 50 slurry of glutathione-sepharose affinity resin (Pharmacia Ltd), pre-equilibrated with 50 mM Tris, 150 mM NaCl, pH 8.0, was added and the bottle was gently rocked for 1–2 hours at room temperature. The resin was then loaded into a 5 ml-column and washed sequentially with 50 mM Tris, 150 mM NaCl, 1% Triton X-100, pH 8.0 and then 50 mM Tris, 100 mM NaCl, pH 8.0, until no further protein was detected in the washings. The bound fusion protein was then eluted from the resin with 50 mM Tris, 150 mM NaCl, 5 mM reduced glutathione, pH 8.0. Fractions (1 ml) were collected and analysed for protein content using the Biorad dye-binding assay for protein (Bradford, (1976) Analytical Biochemistry, 72, pg. 248–254). Fractions showing the peak of protein were bulked prior to further analysis.

2. Antiserum Production

A fusion protein, consisting of the wheat brittle-2 protein sequence linked to glutathione-s-transferase was prepared from transformed *E. coli* cells as described above. This preparation of protein was dialysed against three changes of 50 mm Tris, pH 8.0 and made up to three aliquots, one of 100 µg of protein and two of 50 µg of protein, in 500 µg of 50 mM Tris, pH 8.0. The 100 µg aliquot was mixed with an equal volume of Freund's complete adjuvant and injected subcutaneously into the flank of a New Zealand white rabbit. Each of the two 50 µg aliquots of protein were mixed with an equal volume of Freund's incomplete adjuvant and injected into the same rabbit 4 and 8 weeks after the initial injection. Blood was collected 12 weeks after the primary injection and the cells separated from the serum by clotting and centrifugation. The serum was retained and stored at −20° C.

Identification of Wheat Brittle2 Protein in Transgenic Plants

The following procedure was used to identify wheat brittle-2 protein accumulated in tubers of transformed potato plants.

1. Sodium Dodecylsulphate-polyacrylamide Gel Electrophoresis

Electrophoresis of protein samples was routinely performed using the Schagger and von Jagow system (Analytical Biochemistry (1987), 166, pg. 368–379). Protein extracts were prepared by homogenising tuber tissue (50–100 mg) in an extraction buffer consisting of 50 mM N-2-hydroxyethylpiperazine-N'-2-ethanesulphonic acid (Hepes), pH 8.0; 10 mM diaminoethane tetra-acetic acid (EDTA); 10 mM dithiothreitol (DTT). Protein samples, containing up to 100 µg of protein were prepared by precipitating with acetone, followed by resuspension in water (50 µl) and 2× sample loading buffer (50 µl). Samples were boiled for 60 seconds prior to loading on the gel and were subjected to electrophoresis at 50–60V (constant) for approximately 20 hours. 2× sample loading buffer consisted of 100 mM Tris, pH 6.8; 8% (w/v) sodium dodecylsulphate (SDS); 24% (w/v) glycerol; 4% (v/v) beta-mercaptoethanol; 0.02% (w/v) Coomassie blue.

2. Electroblotting of Proteins

Proteins separated by SDS polyacrylamide gel electrophoresis were transferred onto Immobilon-P PVDF membrane (Millipore) by electroblotting. Membrane, Whatman 3 mm paper and sponges were pre-equilibrated in transfer buffer (25 mM Tris; 192 mM glycine; 20% methanol; pH 8.3) before use. Gels were placed in close contact with membrane, and assembled into transfer cassettes in the specific arrangement given in the manufacturers instructions. Cassettes were placed into an electroblotting tank containing transfer buffer and transfer of proteins from gel to membrane facilitated by applying 50V at 4° C. for 3–4 hours. Blotting was monitored by using prestained protein molecular weight markers (Sigma Chemical Co.).

3. Immunodetection of Immobilised Proteins

Specific proteins were detected on Immobilon-P membranes by using antibodies raised against proteins expressed in *E. Coli*. Membranes were taken directly from the electroblotting tank and placed in a glass dish. The membranes were rinsed briefly with phosphate buffered saline (PBS, 10 mM sodium dihydrogen phosphate ($NaH_2PO_4$); 150 mM NaCl; pH 7.2) and the remaining protein binding sites were blocked by treating with 4% (w/v) bovine serum albumin (BSA) in PBS for 30 minutes. Then membranes were challenged with primary antibody, at a suitable dilution (typically 1/1000–1/10000 (v/v)) in PBS containing 4% BSA for 16 hours at room temperature and with gentle shaking. Excess primary antibody was removed by washing the membranes with several changes of PBS. Membranes were then treated with 20–40 µg of alkaline phosphatase conjugated anti-rabbit IgG (immunoglobulin G) in up to 200 ml of PBS containing 2% (w/v) BSA for 2–3 hours. Unbound conjugate was removed after incubation by washing with several changes of 1% (v/v) Triton X-100 in PBS. Membranes were then washed briefly with 100 mM diethanolamine buffer, pH 9.8 and developed by incubating with alkaline phosphatase reaction mixture (120 µM nitroblue tetrazolium; 135 µM 5-Bromo-4-chloroindolyl phosphate; 4 mM magnesium chloride ($MgCl_2$); 100 mM diethanolamine; pH 9.8). Reaction was allowed to occur until purple-blue bands were visualised, usually after 15–30 minutes. Reaction was stopped by rinsing the membranes under reverse osmosis (RO) water. Membranes were allowed to dry face down on filter paper and stored in the dark.

Assay of ADPG PPase in Transgenic Potatoes

1. Preparation of Extracts

Potato tuber tissue, 2–3 g, was homogenised with 3 ml of extraction buffer (50 mM Hepes, pH 8.0; 10 mM EDTA; 10 mM DTT; 10% (w/v) BSA) using a pestle and mortar. The extract was clarified by centrifugation. To de-salt the extract 2.5 ml of the clarified extract was loaded onto a PD10 gel filtration column (Pharmacia Ltd) pre-equilibrated with extraction buffer, and eluted with 3.5 ml of extraction buffer. This preparation was taken for enzyme assay.

2. Enzyme Assay

The principle of the enzyme assay is as follows:

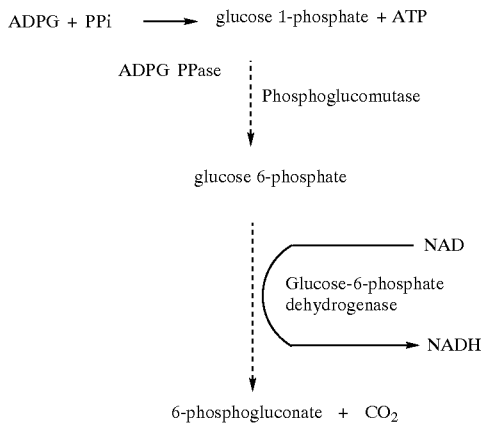

NADH was detected spectrophotometrically at 25° C. and 340 nm.

To a plastic cuvette, in a final volume of 1 ml was taken:

40 mM Hepes, pH 8.0

10 mM magnesium chloride ($MgCl_2$)

1 mM tetra-sodium pyrophosphate ($Na_4P_2O_7$)

0.4 mM nicotinamide adenine dinucleotide (NAD)

4 units glucose-6-phosphate dehydrogenase 2 units phosphoglucomutase

24 $\mu$M glucose 1,6-diphosphate (Glc-1,6-$P_2$) up to 300 $\mu$l of extract

The reaction was started by adding adenosine diphosphoglucose (ADPG) to a final concentration of 0.8 mM.

Analysis of Specific Gravity of Transgenic Potatoes

Whole tubers were weighed in air and under water. The specific gravity was calculated as:

$$\frac{\text{weight in air}}{\text{weight in air} - \text{weight in water}}$$

Analysis of Starch Content of Transgenic Potatoes

Tuber tissue (40–70 mg) was extracted in 500 $\mu$l of 45% $HClO_4$. An aliquot of this extract (50 $\mu$l) was made up to 1 ml with 400 mM Hepes, pH 8.0 and then split into two 500 $\mu$l portions which were both made up to 1 ml by the addition of 400mM Hepes, pH 8.0. To one portion was then added 100 units alpha-amylase and 7 units amyloglucosidase, no enzymes were added to the other portion and both were left overnight before assaying for glucose.

The glucose assay was performed spectrophotometrically at 25° C. and 340 nm.

To a plastic cuvette, in a final volume of 1 ml was taken:

100 mM Hepes, pH 8.0

4 mM $MgCl_2$ 4 mM NAD 3 mM adenosine triphosphate (ATP)

3 units glucose-6-phosphate dehydrogenase from Leuconostoc (Boehringer Mannheim)

500–300 microliters of starch digest.

The reaction was started with 0.3 units of yeast hexokinase (Boehringer Mannheim).

The amount of starch present in the potato tissue can be calculated from the amount of glucose measured in the assay.

The following results were obtained using the above methods.

1. Recognition of Proteins by Anti-Brittle-2 Antiserum in Extracts of Potato and Wheat Extracts of potato tuber and wheat endosperm tissue were prepared according to the methods. Aliquots, containing 100 $\mu$g of protein were taken and run on SDS-PAGE gels as described, blotted and challenged with the anti-brittle-2 antiserum. At a dilution of 1/10000, only one protein band was detected in tracks corresponding to the wheat and potato extracts. Furthermore, the potato band was distinguishable from the wheat band because they were of different sizes. In a third extract, made up of both wheat and potato tissue, two bands were distinguishable, corresponding to the sizes of the bands seen in the individual wheat and potato extracts.

2. Detection of Proteins in Tubers of Potato Plants Transformed with the Gene Sequence for the Wheat Brittle-2 Gene Potato plants were transformed by the leaf disc co-cultivation method with *Agrobacterium tumefaciens* containing the plasmid pFW 4091 containing the DNA coding for the wheat gene for the brittle-2 protein of wheat. Further plants were transformed using the same method and a combination of *Agrobacterium tumefaciens* containing the plasmid pFW 4151 containing the DNA coding for the wheat gene for the shrunken-2 protein of wheat and *Agrobacterium tumefaciens* containing the plasmid pFW 4091 containing the DNA coding for the wheat gene for the brittle-2 protein of wheat. Plasmid pFW 4091 was deposited under accession number NCIMB 40649 and plasmid pFW 4151 was deposited under accession number NCIMB 40650 as described above. Potato tubers from plants which had been transformed with the DNA coding for the wheat gene for the brittle-2 protein of wheat, were analysed for the expression of the gene by Western blotting, as described in the methods, using the antibody raised against the brittle-2glutathione-s-transferase fusion protein. Similarly tubers from lines which had been transformed with brittle-2 and shrunken-2 from wheat were analysed. As described in section 1. above this antiserum recognises a single protein in wheat and a single protein in potato which are distinguishable from each other on the basis of their size. In this way lines were selected which were only expressing the wheat brittle-2 protein. Tubers of these lines were assayed for ADPG PPase activity and starch content as described in the methods, and compared with the activities and starch contents of control tubers.

Figure 3A:
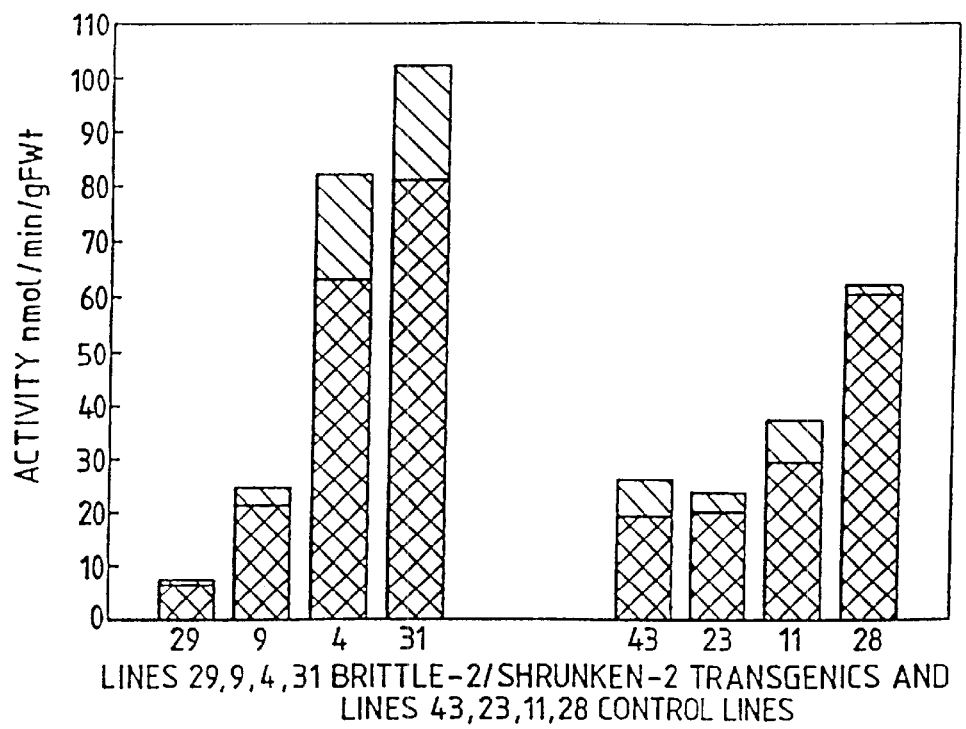
FIG. 3a is a graph of ADPG PPase activity against lines containing the brittle-2 and shrunken-2 genes.
Figure 3B:
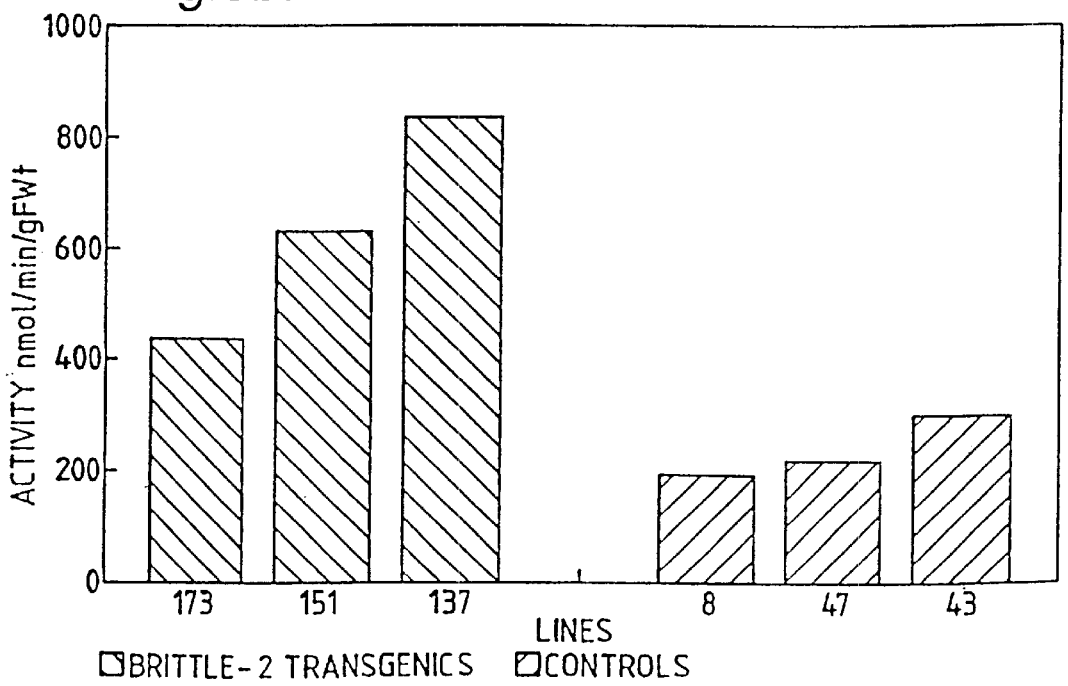
FIG. 3b is a graph of ADPG PPase activity against lines containing the brittle-2 gene.

Fifty lines from tubers treated according to the inventive method were analysed and compared against fifty lines from control (non-treated) tubers. FIGS. 3a and 3b show a selection of the extreme ranges of ADPG PPase activity (namomoles per minute per gram fresh weight) seen in lines which contained the chimaeric gene for brittle-2 and shrunken-2 (FIG. 3a) and in lines containing the chimaeric gene for brittle-2 (FIG. 3b). We believe that these lines show significantly greater ADPG PPase activity than control tubers.

Figure 4:
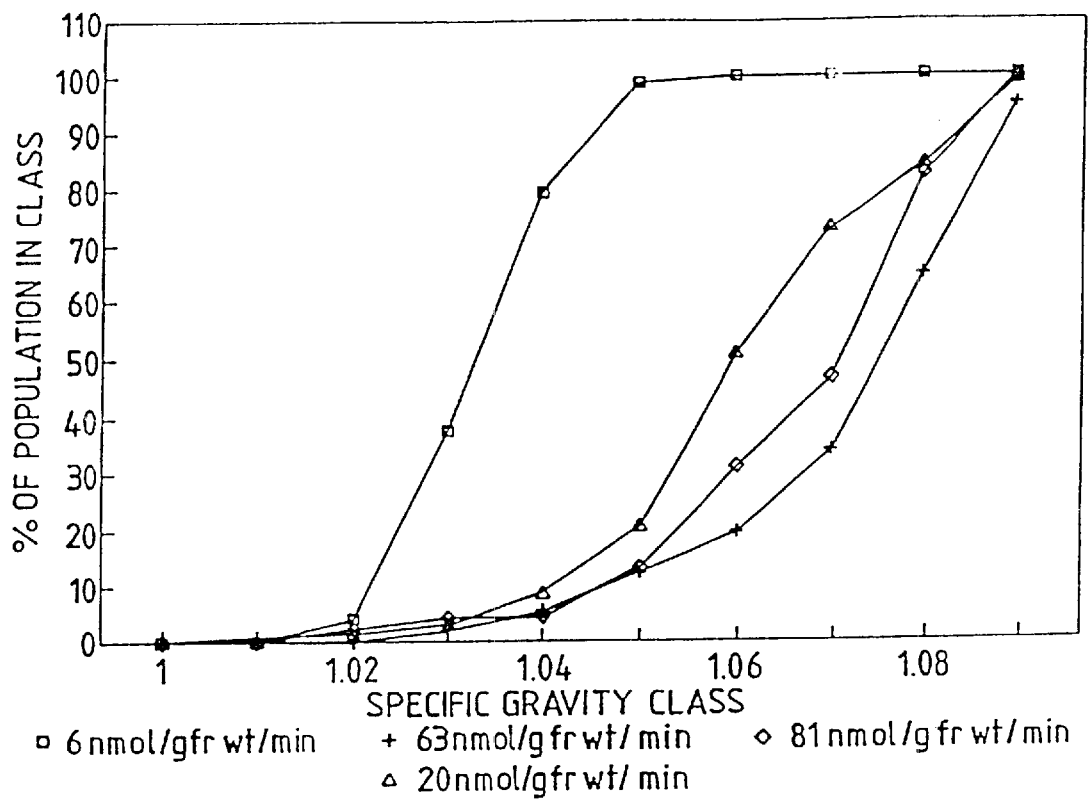
FIG. 4 shows in graphical form the specific gravity of tubers as the cumulative freuquency of tubers in four classes of ADPG PPase activity for lines transformed with brittle-2 and shrunken-2 genes.

FIG. 4 shows in graphical form the specific gravity of tubers as the cumulative frequency of tubers in four classes of ADPG PPase activity for lines transformed with brittle-2 and shrunken-2. A similar analysis for lines transformed with just brittle-2 gives the following change in the median value of the population:

| | | median specific gravity |
|---|---|---|
| transgenic with brittle-2 | line 153 | 1.09 |
| transgenic with brittle-2 | line 32 | 1.095 |
| Control | line 16 | 1.087 |
| Control | line 28 | 1.087 |
| Control | line 38 | 1.089 |

We believe that this increased ADPG production will also lead to increased starch content in the plants as measured by the above described method when grown under appropriate conditions or when suitable other genes are introduced (see below).

Measurement of the Synthesis and Turnover to Starch

To determine the effect of the change in activity on starch synthesis radiolabelled sucrose was supplied to developing tubers of transgenic plants with increased activity of ADPG PPase. Starch was extracted as described above and the radioactivity determined by liquid scintillation counting. A line transformed with brittle-2 gene with elevated ADPGp pase activity was compared to a control line and gave the following result:

| | % Total Counts incorporated into starch | |
|---|---|---|
| | mean | sem |
| brittle-2 line | 0.52 | 0.37 |
| control ine | 0.30 | 0.18 | sem = standard error of mean

Figure 5:
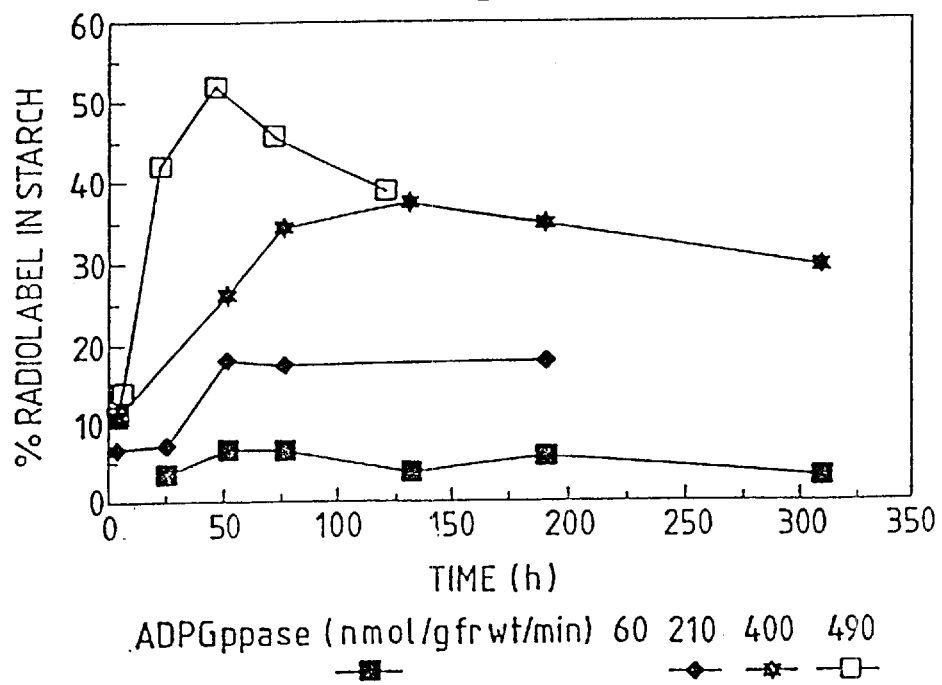
FIG. 5 shows starch synthesis against four lines of different ADPG PPase activity.

To confirm this observation a further experiment with four lines showing different activities of ADPG PPase was used (see FIG. 5). The results in FIG. 5 show that the starch is more rapidly synthesised but show that under certain conditions the starch is more rapidly broken down. Therefore we suggest that this shows that for the invention to be universally applicable it is necessary to introduce operative genes to increase the activity of ADPG PPase and operative genes to decrease the activity of amylase (EC 3.2.1.1 and EC 3.2.1.2) and starch phosphorylase (EC 2.4.1.1).

What is claimed is:

1. A transgenic plant that is not homozygous for a mutant adenosine diphosphoglucose pyrophosphorylase (ADPG PPase), said transgenic plant comprising recombinant nucleic acid encoding only one of the subunit proteins of a heterotetrameric ADPG PPase enzyme, wherein said recombinant nucleic acid has been introduced into the cells of said plant or ancestors thereof such that said subunit is expressed, thereby increasing said ADPG PPase activity in said plant.

2. The plant according to claim 1, wherein said cells of said plant each comprise at least one copy of said recombinant nucleic acid which comprises a shrunken-2 gene or homolog thereof.

3. The plant according to claim 1, wherein said cells of said plant each comprise at least one copy of said recombinant nucleic acid which comprises a brittle-2 gene or homolog thereof.

4. The plant according to claim 1, which is a potato, tomato, cassava, peanut, bean, or pea plant.

5. The plant according to claim 1, which is a wheat, barley, rye, maize, or rice plant.

6. The plant according to claim 3, which is a potato, tomato, cassava, peanut, bean, or pea plant.

7. The plant according to claim 3, which is a wheat, barley, rye, maize, or rice plant.

8. The plant according to claim 3, which is a potato, tomato, cassava, peanut, bean, or pea plant.

9. The plant according to claim 3, which is a wheat, barley, rye, maize, or rice plant.

10. A transgenic plant that is not homozygous for a mutant adenosine diphosphoglucose pyrophosphorylase (ADPG PPase), said transgenic plant comprising recombinant nucleic acid encoding only one of the subunit proteins of a heterotetrameric ADPG PPase enzyme, wherein said subunit is from wheat, and wherein said recombinant nucleic acid has been introduced into the cells of said plant or ancestors thereof such that said subunit is expressed, thereby increasing said ADPG PPase activity in said plant.

\* \* \* \* \*

UNITED STATES PATENT AND TRADEMARK OFFICE
CERTIFICATE OF CORRECTION

PATENT NO. : 6,486,383 B1
DATED : November 26, 2002
INVENTOR(S) : Burrell et al.

It is certified that error appears in the above-identified patent and that said Letters Patent is hereby corrected as shown below:

Column 1,
Line 53, "Adenosine diphosphoglucose pyrophosphorylase" should be on the first line of the paragraph below the flow diagram and not form part of the flow diagram as has been printed in the published patent.

Column 2,
Line 53, change ";gene" to -- gene --.

Column 5,
Line 16, change "pear" to -- pea --.
Line 42, change "tranformation" to -- transformation --.
Line 58, change "50 $\mu$g ml$^{-1}$" to -- 500 $\mu$g ml$^{-1}$ --.

Column 6,
Line 4, change "stock-" to -- stock --.
Line 55, change "CTA TT" to -- CTA TTT --.
Line 57, add -- (SEQ ID NO: 1) -- following "GGA"
Line 59, change "5 ºC" to -- 50 ºC --.

Column 7,
Line 4, change "PPASE" to -- PPase --.
Line 7, change "(Phamacia Ltd.)" to -- (Pharmacia Ltd.) --.
Line 26, change "of a 50" to -- of a 50% --.
Line 33, change "100 mM NaCl" to -- 150 mM NaCl --.
Line 46, change "50 mm" to -- 50 mM --.
Line 47, change "in 500 $\mu$g" to -- in 500 $\mu$l --.

Column 8,
Line 45, change "$^{20\text{-}40}$ mg" to -- 20-40 $\mu$l --.

Column 9,
Line 59, change "1 ml" to -- 1 ml --.

UNITED STATES PATENT AND TRADEMARK OFFICE
CERTIFICATE OF CORRECTION

PATENT NO.    : 6,486,383 B1
DATED         : November 26, 2002
INVENTOR(S)   : Burrell et al.

It is certified that error appears in the above-identified patent and that said Letters Patent is hereby corrected as shown below:

Column 10,
Line 41, change "brittle-2glutathione-s-transferase" to -- brittle-2/glutathione-s-transferase --.

Column 11,
Line 22, change "ADPGppase" to -- ADPG PPase --.

Column 14,
Lines 19 and 21, change "claim 3" to -- claim 2 --.

Signed and Sealed this

Thirteenth Day of May, 2003

JAMES E. ROGAN
*Director of the United States Patent and Trademark Office*